United States Patent [19]

Weisser

[11] 4,002,162
[45] Jan. 11, 1977

[54] LIP AND CHEEK EXPANDER AND TONGUE RETRACTOR WITH TORTIONALLY ADJUSTABLE SPRING MEANS

[76] Inventor: Jacob I. Weisser, 28-15 Fair Lawn Ave., Fair Lawn, N.J. 07410

[22] Filed: Apr. 26, 1976

[21] Appl. No.: 680,433

[52] U.S. Cl. .................................. 128/17; 128/15
[51] Int. Cl.² ......................................... A61B 1/32
[58] Field of Search .................. 128/345, 12–20; 32/40, 33, 35

[56] References Cited
UNITED STATES PATENTS

| 903,344 | 11/1968 | Wackler | 128/12 |
| 1,389,436 | 8/1921 | Cameron | 128/17 |
| 3,241,550 | 3/1966 | Galarie | 128/12 |

FOREIGN PATENTS OR APPLICATIONS

| 317,149 | 12/1902 | France | 128/17 |

Primary Examiner—Robert W. Michell
Assistant Examiner—Henry S. Layton
Attorney, Agent, or Firm—Silverman and Jackson

[57] ABSTRACT

The present invention provides for a lip and cheek expander and tongue retractor for mechanically holding open a patient's mouth and stabilizing his tongue therein so as to facilitate dental and medical procedures. The present expander-retractor comprises first and second arc-shaped shells, each of said shells having a trough-shaped cross-section including first and second side walls; and a spring element having two ends, one of each of said ends secured to the first and second shells respectively, said element disposed in a plane which is substantially transverse to those planes defined by said side walls and which, upon insertion is substantially co-planer with the plane of the patient's tongue. The spring element includes a lingual arch which is adapted for engagement with the paient's tongue. Further, the spring element exhibits a resilient torque which is directed radially outward with respect to the radius of curvature of the arc-shaped shells, whereby the lips of the patient are engaged within said troughs and the tongue of the patient is engaged by the lingual arch of the spring element, thereby significantly assisting the dentist or physician with respect to visual and physical access to the dental area and aiding him in maintaining a clean, dry field of operation.

8 Claims, 6 Drawing Figures

LIP AND CHEEK EXPANDER AND TONGUE RETRACTOR WITH TORTIONALLY ADJUSTABLE SPRING MEANS

BACKGROUND OF THE INVENTION

The prior art has long testified to the need for a dental device which would serve to readily withdraw or expand the lips and cheeks and retract the tongue from their normal position in order to facilitate both a visual and physical access to the teeth as well as to other anatomical areas such as the gingivae surrounding the teeth and the palate and throat, and simultaneously aid him to maintain a clean, dry field of operation without the assistance of an auxiliary person.

The prior art in the present area is represented by such patents as U.S. Pat. No. 2,535,005 (1950) to Wiprud and U.S. Pat. No. 3,916,880 (1975) to Schroer. The devices of said patents, as well as others known in the art, have been found to be awkward of use, in most instances requiring an assistant to hold the instrument in place, and also to involve discomforture on the part of the patient. In addition, certain sterilization problems have attended the use of various prior devices including that of the patent to Schroer. Further, prior devices of the present class have been found to be somewhat difficult to manufacture and, accordingly, have been relatively expensive items for the practitioner to purchase.

In light of the above, it may be appreciated that the present invention comprises an effort to provide a simplified mechanical means of lip, cheek and tongue retention that will be both convenient for use by the dentist and comfortable for the patient, and eliminating the services of an assistant who may now be free to perform other essential duties.

SUMMARY OF THE INVENTION

The present device is essentially what is termed an intra-oral self-retaining appliance. That is, it effectuates certain desired functions by virtue of its disposition inside of the mouth of a patient. More particularly, the present lip and cheek expander also imparts a restraint of movement of the tongue, which restraint is anterior and lateral in nature. This serves to retract the tongue to a position which will prevent its interference with various dental procedures, for example, those necessary in the practice of orthodontics while helping to prevent injury from the instrumentation during the application of all dental and surgical treatment.

The present invention makes use of a stainless steel spring-wire frame having a loop-type lingual arch or tongue confining rake. The present device also assists in the retention of cotton rolls on the lingual and buccal surfaces of both sides of the mandibular or lower arches thereby enabling the operator to maintain a dry and sterile field of operation.

The amount of force exerted against the lips and cheeks is easily regulated through the insertion of the end of a round beak pliers inside one or more of the helical coils which are included within the spring element of the device and, gently bending of the lateral arms of the frame in the direction desired for a particular patient, will serve to increase or decrease, depending upon the direction of bend, the amount of lateral force exerted by the spring. It is to be noted that it is not, at any time, necessary to bend the lingual arch of the spring element; only the lateral arms are adjusted.

A primary object of the present invention is to provide a device of the above type which is durable in construction, reliable and efficient in use, and relatively simple and inexpensive to manufacture, utilize and maintain.

Another object of the instant invention is to provide a lip and cheek expander and tongue retractor which engages the upper and lower lips and cheeks while drawing them apart in a firm but gentle manner and at the same time curbs undesirable movements of the tongue, voluntarily or involuntarily, by the patient.

Yet another object of the invention is to provide a lip and cheek expander and tongue retractor which is comfortable for the patient especially during long treatment procedures.

A yet further object is to provide a device of the above type which may be simply formed through the use of two plastic shells in combination with a single length of appropriately bent stainless steel spring wire.

A yet further object of the invention is to provide a lip and cheek expander and tongue retractor in which the device itself is mechanically maintained in a position such that it does hinder the visual or physical access to the oral cavity and precludes the need to be manually held in position by an assistant or nurse.

A further object of the present invention is to provide a lip and cheek expander and tongue retractor having tortionally adjustable tensioning means in order to vary both the pressure against the lips, tongue and cheeks thereby preventing undesirable contact of these parts with the teeth and gingivae or gums.

A yet further object of the present invention resides in the ease and flexibility in which the above-described changes in degree of expansion of the lips are derivable.

A still further object of the present invention resides in the use of a smooth, acrylic or vinyl-type plastic as plastic shells in the present invention, said shells having superior suitability to anatomical interaction with the lips, cheeks and tongue of a patient.

A still further object of the present invention is to provide a lip and cheek expander and tongue retractor of the above class which can be easily sterilized and, accordingly, will not present sanitation problems for the dentist or patient.

Yet further objects of the invention will become evident from the hereinafter set forth description in conjunction with the accompanying drawings.

DETAILED DESCRIPTION OF THE INVENTION

Figure 1:
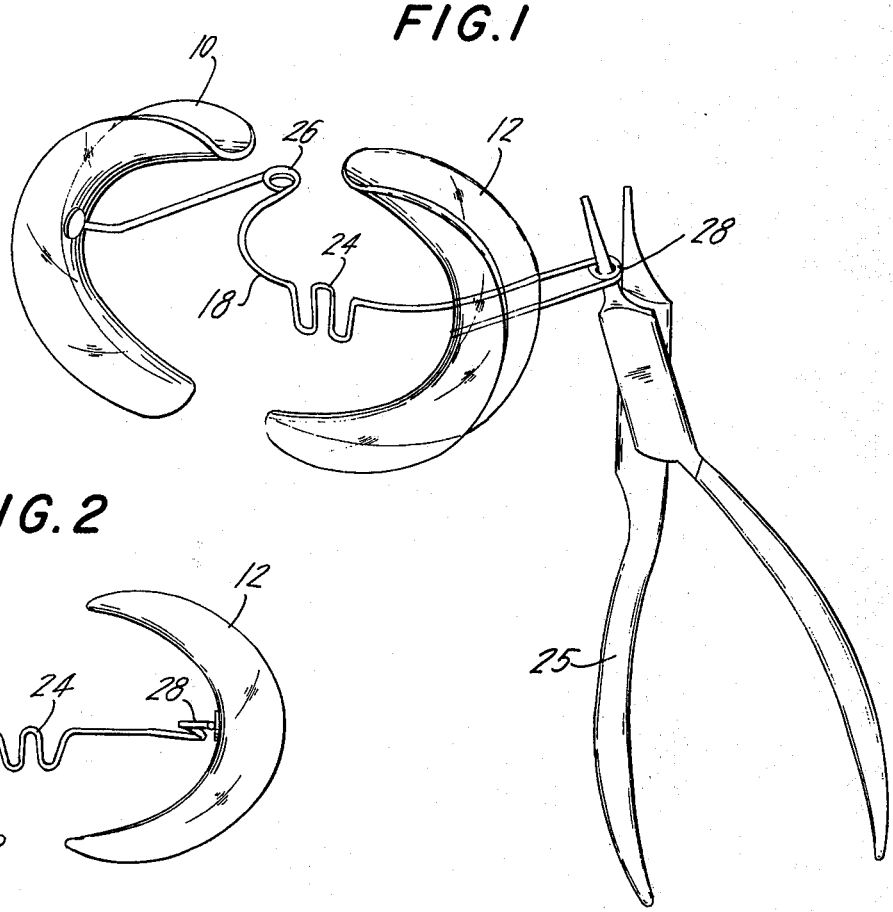
FIG. 1 is a front perspective view of the present invention.
Figure 5:
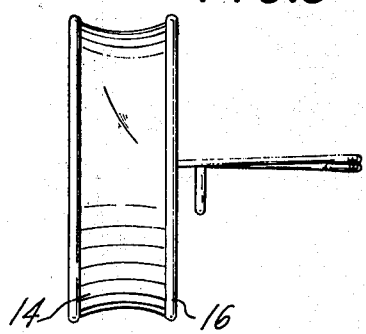
FIG. 5 is a side plan view.

Turning to FIG. 1, one notes that the present lip and cheek expander and tongue retractor includes first and second arc-shaped shells 10 and 12 respectively, each of said shells having a trough-shaped cross-section which includes first and second side walls 14 and 16 respectively (see FIG. 5).

Figure 4:
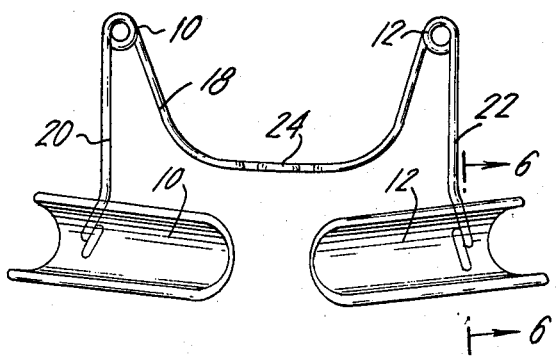
FIG. 4 is a top plan view.
Figure 3:
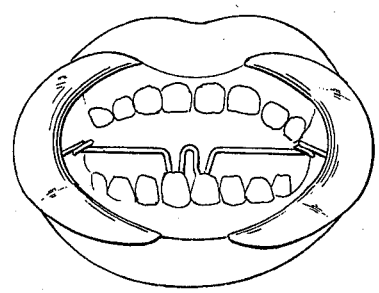
FIG. 3 is a view of the invention disposed within the mouth of a patient.
Figure 6:
FIG. 6 is a cross-sectional view through the right shell of the invention along lines 6—6 of FIG. 4.

The present invention also includes a spring element 18 having two ends 20 and 22 (see FIG. 4) wherein one of each of said ends is secured to said first and second shells 10 and 12. The spring element 18 is disposed within a plane which is substantially transverse to those planes defined by said side walls 14 and 16. Further, spring element 18, upon its insertion into the oral cavity (see FIG. 3), is substantially co-planer with the plane of the patient's tongue.

It is to be appreciated that spring element 18 includes therein a rake-shaped lingual arch 24 which is particularly adapted for engagement with the patient's tongue. (See FIG. 3). Said lingual arch may be formed in various ways; however, it has been found convenient to form said arch by the making of several bends within the stainless-steel wire of which the spring 18 is preferably formed.

The role of the spring element is that of a resilient element capable of exerting a torque which is directed radially outward with respect to the radius of curvature of the arc-shaped shells 10 and 12. In this process, the lips and intra-oral sides of the cheeks of the patient are engaged within the trough of said shell while the tongue of the patient is engaged within the lingual arch 24. The particular design of the present device, taken in conjunction with the torque action of said spring element, acts to stabilize the tongue in a retracted position while maintaining the lips and cheeks at a lateral bias with respect to the dental and gingival area.

It is to be further noted that the use of a stainless-steel wire frame utilizing the above-described loop-type lingual arch assists in the retention of cotton rolls on the lingual and buccal surfaces of both sides of the mandibular or lower dental arches.

Figure 2:
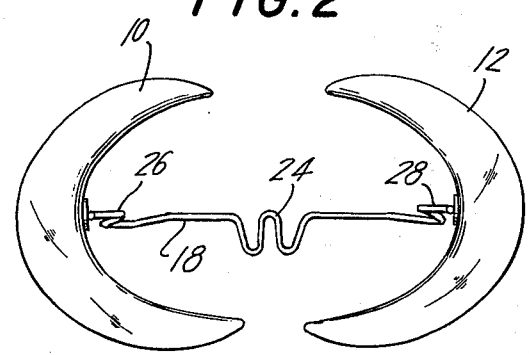
FIG. 2 is a view of the invention showing the use of a round-beak pliers in order to adjust the torque level of the spring element.

The amount of resilience or springiness of the element 18 is easily regulated through the insertion of the round-beak of bending pliers inside of the helical loop 26 and 28 of the spring element 18. See FIG. 2. In order to change the degree or direction of resilience of the spring, the round-beak of the pliers is inserted into the coil and the lateral arms are bent in the direction desired so as to increase or decrease the amount of lateral force which will be applied against the lips and cheeks of the patient. In this process, the cheeks and lips are expanded laterally, superiorly and inferiorly in such a manner that the labial, buccal and lingual surfaces of all teeth are exposed to view.

It is to be noted that the present instrument is readily sterilizable and is free from the possibility of corrosion. The entire instrument is readily cleansible with soap and water and sterilizable in cold sterilizing solution.

Use of the instrument is easily effectuated by compressing the plastic shells, passing the wire frame into the mouth, and releasing the pressure that has been exerted with the thumb and fingers against the plastic shells, until the lips and inner cheeks embrace and encircle the plastic shells. In like manner, removal is achieved by compression of both shells so as to render it readily removeable from the mouth.

The plastic shells are formed of an acrylic or vinyl-type plastic and are extremely smooth so there can be no irritation of the lips or inner cheeks. It has been found that the present instrument can be retained in the mouth for periods that are virtually unlimited without any appreciable amount of discomfort or injury to the patient.

A further outstanding feature of the present device is that where formally hand-held lip and cheek expanders required the use of an additional auxiliary person, such as a nurse or dental assistant who had to hold the instrument with two hands while the doctor performed whatever operation was required. The present device is self-retaining within the mouth so that it leaves auxiliary personnel free to perform other duties. It is also quite useful in intraoral photography in that it achieves expansion of the cheeks and lips as well as retraction of the tongue in order to very effectively allow free view of the entire oral cavity.

While there have been herein shown and described the preferred embodiments of the present invention, it will be understood that the invention may be embodied otherwise than as herein specifically illustrated or described and that within said embodiments certain changes in the detail and construction, and the form of arrangement of the parts may be made without departing from the underlying idea or principles of this invention within the scope of the appended claims.

What is claimed is:

1. A lip and cheek expander and tongue retractor for holding open a patient's mouth and stabilizing his tongue therein so as to facilitate dental and medical procedures, said expander-retractor comprising:
    a. first and second arc-shaped shells, each of said shells having a trough-shaped cross-section including first and second side walls; and
    b. a spring element having two ends, one of each of said ends secured to said first and second shells respectively, said element disposed in a plane which is (i) substantially transverse to those planes defined by said side walls and is (ii) upon insertion into the oral cavity, substantially co-planer with the plane of the patient's tongue, said spring element including a lingual arch adapted for tongue engagement, said spring element further having a resilient torque which is directed radially outward with respect to the radius of curvature of said arc-shaped shells,
    whereby the lips and cheeks of a patient are engaged within the troughs of said shells and the tongue of said patient is engaged within said rake-like lingual arch such that, through the torque action of said spring element, the tongue is stabilized in a retracted position while the lips and cheeks are biased laterally outward with respect to the dental area.

2. The retractor as defined in claim 1 in which said spring element includes a plurality of coiled loops having diameters which are suitable to gripping and adjustment by a round-beak pliers.

3. The expander-retractor as recited in claim 2 in which said spring element is formed of non-corrosive metal wire.

4. The retractor as recited in claim 3 in which said lingual arch comprises a segment of said metal wire formed in the shape of the letter "C" including a downward loop to retract the tongue in a rake-like manner.

5. The expander-retractor as recited in claim 3 in which said lingual arch comprises a segment of said metal wire formed in the shape of the letter "W".

6. The expander-retractor as recited in claim 3 in which said metal is non-corrosive stainless steel.

7. The expander-retractor as recited in claim 3 in which said plurality of coils comprises two coils.

8. The retractor as recited in claim 7 in which said arc-shaped shells are formed of an acrylic or vinyl type plastic.

* * * * *